United States Patent [19]

Large

[11] 4,384,880
[45] * May 24, 1983

[54] TRIALKYLSULFONIUM SALTS OF N-PHOSPHONOMETHYL-GLYCINE AND THEIR USE AS PLANT GROWTH REGULATORS AND HERBICIDES

[75] Inventor: George B. Large, Orinda, Calif.

[73] Assignee: Stauffer Chemical Company, Westport, Conn.

[*] Notice: The portion of the term of this patent subsequent to Feb. 16, 1999, has been disclaimed.

[21] Appl. No.: 324,283

[22] Filed: Nov. 25, 1981

Related U.S. Application Data

[63] Continuation-in-part of Ser. No. 212,921, Dec. 4, 1980, Pat. No. 4,315,765.

[51] Int. Cl.³ .................. C07F 9/38; A01N 57/00
[52] U.S. Cl. .................... 71/87; 260/502.5 F
[58] Field of Search .................. 260/502.5; 71/87

[56] References Cited

U.S. PATENT DOCUMENTS

| | | | |
|---|---|---|---|
| 2,854,791 | 10/1958 | Antognini | 47/58 |
| 3,101,265 | 8/1963 | Smutny et al. | 71/2.7 |
| 3,235,356 | 2/1966 | Herschler | 71/2.3 |
| 3,652,255 | 3/1972 | Osieka et al. | 71/76 |
| 3,799,758 | 3/1974 | Franz | 71/86 |
| 3,835,000 | 9/1974 | Frazier et al. | 204/78 |
| 3,853,530 | 12/1974 | Franz | 71/76 |
| 3,929,450 | 12/1975 | Hamm et al. | 71/86 |
| 3,977,860 | 8/1976 | Franz | 71/86 |
| 3,988,142 | 10/1976 | Franz | 71/86 |
| 4,059,431 | 11/1977 | Takematsu et al. | 71/87 |
| 4,059,432 | 11/1977 | Takematsu et al. | 71/87 |
| 4,147,719 | 4/1979 | Franz | 260/501.12 |
| 4,251,259 | 2/1981 | Preziuso et al. | 71/88 |
| 4,315,765 | 2/1982 | Large | 260/502.5 F |

*Primary Examiner*—Joseph E. Evans
*Attorney, Agent, or Firm*—Harry A. Pacini

[57] ABSTRACT

Novel trialkylsulfonium salts of N-phosphonomethylglycine are disclosed herein, having the formula

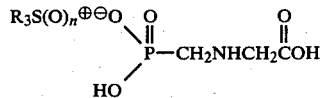

in which R represents $C_1$–$C_3$ alkyl and n is zero or one. The compounds are useful in regulating the natural growth or development of plants and as herbicides.

6 Claims, No Drawings

TRIALKYLSULFONIUM SALTS OF N-PHOSPHONOMETHYL-GLYCINE AND THEIR USE AS PLANT GROWTH REGULATORS AND HERBICIDES

CROSS REFERENCE TO RELATED APPLICATION

This is a continuation-in-part of application Ser. No. 212,921, filed Dec. 4, 1980 now U.S. Pat. No. 4,315,765.

BACKGROUND OF THE INVENTION

This invention is directed to novel chemical compounds and their use in regulating the natural growth or development of plants. In particular, this invention relates to the chemical treatment of plants to alter their natural growth or development for the purpose of enhancing various agricultural or horticultural features of the plants, and also to the control of undesirable vegetation.

It is well known among those skilled in the art of agriculture and horticulture that various features of plant growth can be modified or regulated to produce a variety of beneficial effects.

For instance, certain types of treatment can produce defoliation of a plant in a beneficial manner, i.e., inhibiting further leaf growth while permitting further development of the productive plant parts. As a result, the productive parts demonstrate extra growth, and subsequent harvesting operations are facilitated. Defoliants are particularly useful in flax, cotton, and bean crops, and other crops of a similar nature. Although defoliation results in the killing of leaves, it is not a herbicidal action per se since the remainder of the plant is unharmed. Indeed, killing of the treated plant is undesirable when defoliation is sought, since leaves will continue to adhere to a dead plant.

Another response demonstrated by plant growth regulants is the general retardation of vegetative growth. This response has a wide variety of beneficial features. In certain plants it causes a diminution or elimination of the normal apical dominance, and thus leads to a shorter main stem and increased lateral branching. This alteration of the natural growth or development produces smaller, bushier plants which often demonstrate increased resistance to drought and pest infestation. The retardation of vegetative growth in turf grasses is particularly desirable. When the vertical growth rate of such grasses is lessened, root development is enhanced and a denser, sturdier turf is produced. The retardation of turf grasses also serves to increase the interval between mowings of lawns, golf courses and similar grassy areas.

In many types of plants, such as silage crops, potatoes, sugar cane, beets, grapes, melons and fruit trees, the retardation of vegetative growth results in an increase in the carbohydrate content of the plants at harvest. It is believed that the retardation or suppression of such growth at the appropriate stage of development causes less of the available carbohydrate to be consumed for vegetative growth and results in an enhanced starch and/or sucrose content. Retardation of vegetative growth in fruit trees is demonstrated by shorter branches and greater fullness of shape, and often results in lesser vertical elongation. These factors contribute to the ease of access to the orchard and simplify the fruit harvesting procedure.

BRIEF DESCRIPTION OF THE INVENTION

It has now been discovered that novel trialkylsulfonium salts of N-phosphonomethylglycine are useful in both regulating the natural growth or development of plants and in controlling undesirable vegetation. These salts have the formula

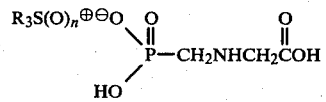

where R represents $C_1$–$C_3$ alkyl, and n is zero or one.

This invention further relates to a method of regulating the natural growth or development of plants comprising applying to said plants an effective, plant-regulating, non-lethal amount of the above compounds, as well as a method of controlling undesirable vegetation comprising applying a herbicidally effective amount of the compounds to such vegetation when the latter is in a postemergence state.

As employed herein, the term "natural growth or development" designates the normal life cycle of a plant in accordance with its genetics and environment, in the absence of artificial external influences. A preferred utility of the instant compounds is in increasing the sucrose yield of field grown sugarcane and sorghum. The term "regulating" is used herein to denote the bringing about through chemical means of any temporary or permanent modification or variation from the normal life cycle short of killing the plant.

The term "herbicidally effective amount" designates any amount of the compounds disclosed herein which will kill a plant or any portion thereof. By "plants" is meant germinant seeds, emerging seedlings, and established vegetation, including roots and above-ground portions. Herbicidal effects include killing, defoliation, desiccation, stunting, leaf burn, and dwarfing. Herbicidal effects are generally achieved at higher application rates than growth regulating effects.

The term "alkyl" is used herein to include both straight-chain and branched-chain alkyl groups. The carbon atom range is intended to be inclusive of its upper and lower limits.

Examples of specific compounds falling within the above formula are:
trimethylsulfonium salt of glyphosate
trimethylsulfoxonium salt of glyphosate
triethylsulfonium salt of glyphosate
triethylsulfoxonium salt of glyphosate
tripropylsulfonium salt of glyphosate
tripropylsulfoxonium salt of glyphosate

DETAILED DESCRIPTION OF THE INVENTION

In accordance with the instant invention, regulation of the natural growth or development of plants is achieved by the direct application of a compound within the above formula or a formulation of such a compound to the plants or to any of their above-ground portions at approximately 4 to 10 weeks prior to harvest. With properly controlled application, a growth regulating effect can be achieved without herbicidal results. The amount which constitutes an effective amount varies not only with the particular material selected for treatment, but also with the regulatory effect to be achieved, the species of plant being treated and its stage of development, and whether a permanent or transient effect is sought. Other factors which bear upon the determination of an appropriate plant regulating amount include the manner of application and weather conditions such as temperature or rainfall. Growth regulation may arise from the effect of the compound on either the physiological processes or the morphology of the plant, or from both in combination or in sequence. Morphological changes are generally noticeable by observable changes in the size, shape, color or texture of the treated plant or any of its parts, as well as in the quantity of fruit or flowers produced.

Changes in physiological processes, on the other hand, occur within the treated plant and are usually hidden from the eye of an observer. Changes of this type most often occur in the production, location, storage or use of chemicals naturally occurring in the plant, such as hormones. Physiological changes may be visually detectable when followed by a change in morphology. In addition, numerous analytical procedures for determining the nature and magnitude of changes in the various physiological processes are known to those skilled in the art.

The compounds of the instant invention serve to regulate the natural growth or development of treated plants in a number of diverse ways, and it is to be understood that each compound may not produce identical regulatory effects on each plant species or at every rate of application. As stated above, responses will vary in accordance with the compound, the rate, the plant, etc.

Herbicidal effects are achieved in a similar manner, and the strength of the application can be varied to achieve the desired result.

The compounds of this invention are readily prepared from N-phosphonomethylglycine by reacting the latter with silver oxide to form the silver salt or with sodium hydroxide to form the sodium salt, and treating either the silver or sodium salt with a trialkylsulfonium or -sulfoxonium halide. Alternatively, the glycine can be reacted directly with the trialkylsulfonium or -sulfoxonium halide in the presence of propylene oxide. N-Phosphonomethylglycine is a commercially available material known by the common name "glyphosate." It can be prepared by the phosphonomethylation of glycine, the reaction of ethyl glycinate with formaldehyde and diethylphosphite, or the oxidation of the N-phosphinomethylglycine. Such methods are described in U.S. Pat. No. 3,799,758 (Franz, Mar. 26, 1974).

As illustrated in the examples which follow, the compounds of the invention can either regulate the natural growth or development of plants or kill weeds. While regulatory responses are often desirable in their own right, their effect on crop economics is most often of primary significance. Thus, increases in the yield of individual plants, increases in the yield per unit area, and reductions in the cost of harvesting and/or subsequent processing are all to be considered in assessing the consequence of an individual regulatory effect during the growth or development of a plant.

The specific examples which follow are presented as merely illustrative, non-limiting demonstrations of the preparation of the compounds of the instant invention and of their effectiveness in regulating the growth of plants and in controlling undesirable vegetation.

EXAMPLE 1

Mono-Trimethylsulfonium Salt of Glyphosate

A solution was prepared consisting of 80 ml of tetrahydrofuran and 20 ml of water. To this solution was added 1.7 g (0.01 mole) of N-phosphonomethylglycine, obtained from Monsanto Agricultural Products, Co., St. Louis, Mo., and 0.4 g (0.01 mole) of powdered sodium hydroxide. Then 2.0 g (0.01 mole) of trimethylsulfonyl iodide was added and a clear solution resulted. The solution was then stripped of volatiles, dispersed in ethanol, and heated to 60° C. Filtration and drying produced 1.8 g of a white powder, whose molecular structure was confirmed by carbon-13 and proton nuclear magnetic resonance as that of the mono-trimethylsulfonium salt of N-phosphonomethylglycine.

EXAMPLE 2

Mono-Trimethylsulfoxonium Salt of Glyphosate

A reaction vessel was charged with 50 ml of water, 4.2 g (0.025 mole) of N-phosphonomethylglycine, and 5.5 g (0.025 mole) of trimethylsulfoxonyl iodide. The vessel was heated gently in a water bath and 15 ml of propylene oxide was added. The mixture was stirred for one hour then washed with ether and phase separated. The aqueous phase was then stripped, yielding 5.8 g of a white powder with a melting point range of 184°–186° C. The molecular structure of the product was confirmed by carbon-13 and proton nuclear magnetic resonance as that of the mono-trimethylsulfoxonium salt of N-phosphonomethylglycine.

Other compounds within the scope of the generic formula shown above can be prepared by either of these methods with appropriate starting materials.

EXAMPLE 3

This example illustrates the utility of the compound prepared in Example 1 in regulating the growth of sweet sorghum (scientific name: *Sorghum vulgare*).

The following test procedure was used:

A series of white plastic pots, 7.5 inches (19.0 cm) in diameter, were filled with approximately 10 pounds (4.54 kilograms) each of sandy loam soil containing 100 parts per million (ppm) of cis-N[(trichloromethyl)thio]-4-cyclohexene-1,2-dicarboximide (a commercially available fungicide) and 150 ppm of 17-17-17 fertilizer (i.e., comprising 17% by weight each of N, $P_2O_5$, and $K_2O$). Eight sorghum seeds were placed in each pot and the pots were placed in a greenhouse in which the temperature was maintained at 27° C. during the day and 21° C. at night. During the next five weeks, the emerging plants were thinned down to one per pot. The pots were fertilized periodically with 17-17-17 fertilizer.

The plants were sprayed 114 days after seeding with a solution consisting of the test compound dissolved in equal portions of acetone and water. The spraying system was pressurized by carbon dioxide and mounted on a bicycle-type apparatus. The test solution was sprayed at a rate of 80 gallons per acre (750 liters per hectare). The concentration of the solution was pre-determined to produce the desired application rate in pounds per acre (lb/A) when sprayed on the plants at a total volume of 80 gallons per acre. The concentration was thus selected to correspond to an application rate of 0.25 lb/A (0.28 kilograms per hectare).

Following treatment, the plants were placed in the greenhouse for an additional 39 days. During this time, the degree of seedhead emergence and pollen shedding were recorded periodically. The plants were then harvested. The stalks were cut at soil level and the seedhead and peduncle were removed. For each stalk, the seedhead was dried and then weighed, and the peduncle length was measured. The remainder of the stalk was then stripped of all leaves and leaf sheaths, and its length and weight were determined. The stalks were then chopped into small segments and squeezed in a hydraulic press at a pressure of 20,000 pounds per square inch (13,800 Newtons per square centimeter). The quantity of the expressed juice was measured as well as its quality in terms of total dissolved solids. The latter was measured with a hand juice refractometer, and is expressed as weight percent of the juice.

Five replications were performed at each application rate. In addition, five untreated plants were included as check plants for comparison. The results are shown in Tables I and II.

Table I lists the data pertaining to seedhead emergence and pollen shedding. The data listed are averages of each set of five replications. It is clear in each case that both the extent of seedhead emergence and pollen shedding were reduced when the test solutions were applied. This reduction in flowering is one indication of an increase in the efficiency of sucrose production and storage.

Table II lists averages of the measurements taken on the seedhead, peduncle, stalk, and expressed juice after the harvesting of the plants. The data indicate a reduction in the dried seedhead weight, the peduncle lengths, and the height and weight of the stalk, as compared to the check plant averages.

TABLE I
PRE-HARVEST DATA
Averages of 5 Replications Each

Test Compound: $(CH_3)_3S^{\oplus} \ ^{\ominus}O\underset{HO}{\overset{}{\diagdown}}\underset{}{\overset{O}{\underset{\|}{P}}}-CH_2NHCH_2\overset{O}{\underset{\|}{C}}OH$ Seedhead Emergence (%) and Pollen Shedding (%)

| Application Rate (lb/A) | \multicolumn{10}{c}{DAYS AFTER SEEDING:} |||||||||| |
|---|---|---|---|---|---|---|---|---|---|---|
| | 121 | | 131 | | 135 | | 138 | | 149 | |
| | SE | PS | SE | PS | SE | PS | SE | PS | SE | PS |
| 0 (check) | 0 | 0 | 20 | 7 | 42 | 33 | 74 | 55 | 93 | 93 |
| 0.25 | 0 | 0 | 0 | 0 | 0 | 0 | 0 | 0 | 0 | 0 |

TABLE II
POST-HARVEST DATA
Averages of 5 Replications Each

Test Compound: $(CH_3)_3S^{\oplus} \ ^{\ominus}O\underset{HO}{\overset{}{\diagdown}}\underset{}{\overset{O}{\underset{\|}{P}}}-CH_2NHCH_2\overset{O}{\underset{\|}{C}}OH$

| Application Rate (lb/A) | Dried Seedhead Weight (g) | Peduncle Length (mm) | Stalk Height (mm) | Stalk Weight (g) | Expressed Juice Amount (g) | Expressed Juice TDS* (wt %) |
|---|---|---|---|---|---|---|
| 0 (check) | 10.2 | 234 | 711 | 94.5 | 18.0 | 13.5 |
| 0.25 | 0.5 | 20 | 490 | 90.2 | 15.6 | 13.4 |

*TDS: Total Dissolved Solids

This example demonstrates the postemergence herbicidal activity of the compounds prepared in Examples 1 and 2.

Aluminum planting flats measuring 15.2×22.9×8.9 cm were filled to a depth of 7.6 cm with loamy sand soil, containing 50 parts per million (ppm) each of the commercial fungicide cis-N[(trichloromethyl)thio]-4-cyclohexene-1,2-dicarboximide (Captan®) and 17-17-17 fertilizer (percentages of $N-P_2O_5-K_2O$) on a weight basis). Several rows were impressed across the width of each flat and a variety of seeds of both grass and broadleaf weed species were planted, one species per row. The weed species used are listed below:

| Broadleaf weeds: | |
|---|---|
| A. Annual mornining glory | Ipomoea purpurea |
| B. Cocklebur | Xanthium sp. |
| C. Jimsonweed | Datura stramonium |
| D. Velvetleaf | Abutilon theophrasti |
| E. Mustard | Brassica sp. |
| F. Nightshade | Solanum sp. |
| G. Pigweed | Amaranthus sp. |
| Grasses: | |
| H. Yellow nutsedge | Cyperus esculentus |
| I. Downybrome | Bromus tectorum |
| J. Foxtail | Setaria sp. |
| K. Annual ryegrass | Lolium multiflorum |
| L. Watergrass | Echinochloa crusgalli |
| M. Shattercane | Sorghum bicolor |
| N. Wild oat | Avena fatua |

The broad leaf species were seeded first, and the grasses were seeded four days later. Ample seeds of each species were planted to produce 20 to 50 seedlings per row after emergence, depending on the size of each plant.

Ten days after the grasses were seeded, the emerged seedlings of all species were sprayed with aqueous solutions of the test compounds. The solutions were prepared to such dilutions that a spray rate of 80 gallons per acre (750 liters per hectare) gave from 0.5 to 4.0 pounds of test compound per acre (0.56 to 4.48 kilograms per hectare) as desired for each test. Additional flats not treated at all were used as standards for measuring the extent of weed control in the treated flats.

Nineteen days later, the test flats were compared to the standards and the weeds in each row were rated visually in terms of percent control ranging from 0% to 100%, with 0% representing the same degree of growth as the same row in the standard and 100% representing complete kill of all weeds in the row. All types of plant injury were taken into consideration. The results are shown in Table III.

TABLE III

HERBICIDAL TEST RESULTS

| Test Compound | Application Rate (lb/A) | Percent Control | | | | | | | | | | | | |
|---|---|---|---|---|---|---|---|---|---|---|---|---|---|---|
| | | Broadleaf Weeds | | | | | | Grasses | | | | | | |
| | | A | B | C | D | E | F | G | H | I | J | K | L | M | N |
| N—phosphonomethyl- glycine, trimethyl- sulfonium salt | 0.5 | 50 | 50 | 60 | 65 | 65 | 75 | 50 | 75 | 40 | 95 | 98 | 65 | 60 | 35 |
| | 1.0 | 65 | 70 | 70 | 70 | 80 | 80 | 70 | 80 | 60 | 100 | 100 | 80 | 95 | 50 |
| | 2.0 | 70 | 100 | 85 | 90 | 100 | 85 | 80 | 80 | 70 | 100 | 100 | 90 | 100 | 65 |
| | 3.0 | 80 | 100 | 100 | 100 | 100 | 95 | 100 | 90 | 75 | 100 | 100 | 100 | 100 | 90 |
| | 4.0 | 95 | 100 | 100 | 100 | 100 | 100 | 100 | 90 | 100 | 100 | 100 | 100 | 100 | 100 |
| N—phosphonomethyl- glycine, trimethyl- sulfoxonium salt | 0.5 | 45 | 40 | 60 | 65 | 65 | 60 | 60 | 65 | 70 | 95 | 95 | 90 | 90 | 70 |
| | 1.0 | 80 | 70 | 100 | 85 | 95 | 90 | 80 | 80 | 80 | 100 | 100 | 100 | 100 | 85 |
| | 2.0 | 90 | 100 | 100 | 95 | 100 | 100 | 100 | 80 | 90 | 100 | 100 | 100 | 100 | 90 |
| | 3.0 | 95 | 100 | 100 | 100 | 100 | 100 | 100 | 85 | 100 | 100 | 100 | 100 | 100 | 100 |
| | 4.0 | 100 | 100 | 100 | 100 | 100 | 100 | 100 | 90 | 100 | 100 | 100 | 100 | 100 | 100 |

EXAMPLE 5

Mono-Triethylsulfonium Salt of Glyphosate

A reaction vessel was charged with 100 ml of water, 4.2 g (0.025 mole) of N-phosphonomethylglycine, and 6.2 g (0.025 mole) of triethylsulfonium iodide. The reaction mixture was heated to 50° C. and stirred at this temperature for one hour. It was then cooled to 15° C. and 15 ml of propylene oxide was added. The resulting mixture was stirred at room temperature for two hours, then washed with ether and phase separated. The aqueous phase was then stripped, redissolved in ethanol, dried with sodium sulfate and washed again with ether. The final yield was 7.5 g of a liquid with a refractive index of $n_D^{30} = 1.5197$. The molecular structure of the product was confirmed by carbon-13 nuclear magnetic resonance and infrared spectroscopy as that of the mono-triethylsulfonium salt of N-phosphonomethylglycine.

EXAMPLE 6

This example demonstrates the postemergence herbicidal activity of the compound prepared in Example 5. The procedure described in Example 4 was used, with the following modifications: the species pigweed was not included; the grass species were seeded three days after the broadleaf species; treatment of the emerged seedlings with the test compound was done eleven days after the grasses were seeded; and injury ratings were taken twenty-one days after treatment. The results are shown in Table IV.

and diluent carriers to aid in their dispersal. Examples of such ingredients or carriers are water, organic solvents, dusts, granules, surface active agents, water-in-oil and oil-in-water emulsions, wetting agents, dispersing agents, and emulsifiers. The formulations generally take the form of dusts, solutions, emulsifiable concentrates, or wettable powders.

A. DUSTS

Dusts are dense powder compositions which combine the active compounds with a dense, free-flowing solid carrier. They are intended for application in dry form and are designed to settle rapidly to avoid being windborne to areas where their presence is not desired.

The carrier may be of mineral or vegetable origin, and is preferably an organic or inorganic powder of high bulk density, low surface area, and low liquid absorptivity. Suitable carriers include micaceous talcs, pyrophyllite, dense kaolin clays, tobacco dust, and ground calcium phosphate rock.

The performance of a dust is sometimes aided by the inclusion of a liquid or solid wetting agent, of ionic, anionic, or nonionic character. Preferred wetting agents include alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Dispersants are also useful in the same dust compositions. Typical dispersants include methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N-(long chain acid) taurates.

In addition, inert absorptive grinding aids are frequently included in dust compositions to aid in the man-

TABLE IV

HERBICIDAL TEST RESULTS

Test Compound: N—phosphonomethylglycine, triethylsulfonium salt

| Application Rate (lb/A) | Percent Control | | | | | | | | | | | | |
|---|---|---|---|---|---|---|---|---|---|---|---|---|---|
| | Broadleaf Weeds | | | | | | Grasses | | | | | | |
| | A | B | C | D | E | F | H | I | J | K | L | M | N |
| 0.25 | 45 | 50 | 35 | 40 | 65 | 60 | 25 | 45 | 100 | 80 | 75 | 50 | 45 |
| 0.5 | 55 | 65 | 40 | 55 | 80 | 90 | 60 | 80 | 100 | 90 | 95 | 100 | 75 |
| 1.0 | 80 | 80 | 55 | 65 | 85 | 95 | 75 | 100 | 100 | 100 | 100 | 100 | 90 |
| 2.0 | 85 | 100 | 65 | 90 | 90 | 100 | 85 | 100 | 100 | 100 | 100 | 100 | 95 |
| 3.0 | 100 | 100 | 90 | 100 | 100 | 100 | 95 | 100 | 100 | 100 | 100 | 100 | 100 |

METHODS OF APPLICATION

Whether used as plant growth regulators or as herbicides, the compounds of the present invention are most useful when applied directly to the plants subsequent to their emergence from the soil. In use at an agricultural field site, the compounds are generally embodied in suitable formulations containing additional ingredients ufacturing of the dust. Suitable grinding aids include attapulgite clay, diatomaceous silica, synthetic fine silica and synthetic calcium and magnesium silicates.

In typical dust compositions, carriers are usually present in concentrations of from about 30 to 90 weight percent of the total composition. The grinding aid usually constitutes about 5 to 50 weight percent, and the wetting agent up to about 1.0 weight percent. Dispersants, when present, constitute up to about 0.5 weight percent, and minor amounts of anticaking and antistatic agents may also be present. The particle size of the entire composition is usually about 30 to 50 microns.

B. SOLUTIONS

Aqueous solutions of the active compounds are prepared such that application at the rate of about 1 to about 200 gallons of solution per acre (about 9 to about 1875 liters per hectare) will provide the required amount of active ingredient. A small amount of nonphytotoxic surfactant typically between 0.05% and 0.5% by weight is usually included to improve the wetting ability of the solution and thus its distribution over the plant surface. Anionic, cationic, nonionic, ampholytic, and zwitterionic surfactants are all useful in this regard.

Suitable anionic surfactants include alkali metal, ammonium, and amine salts of fatty alcohol sulfates having from 8–18 carbon atoms in the fatty chain and sodium salts of alkyl benzene sulfonates having from 9 to 15 carbon atoms in the alkyl chain. Suitable cationic surfactants include dimethyl dialkyl quaternary ammonium halides with alkyl chains of 8 to 18 carbon atoms. Suitable nonionic surfactants include polyoxyethylene adducts of fatty alcohols having 10 to 18 carbon atoms, polyethylene oxide condensates of alkyl phenols with alkyl chains of 6 to 12 carbon atoms and 5 to 25 moles of ethylene oxide condensed onto each mole of alkyl phenol, and polyethylene oxide condensates of sorbitan esters with 10 to 40 moles of ethylene oxide condensed onto each mole of sorbitan ester. Suitable ampholytic surfactants include secondary and tertiary aliphatic amine derivatives with one aliphatic substituent containing 8 to 18 carbon atoms and another containing an anionic water-solubilizing group such as a sulfate or sulfonate. Sodium-3-dodecylaminopropionate and sodium-3-dodecyl amino propane sulfonate are examples. Suitable zwitterionic surfactants include derivatives of aliphatic quaternary ammonium compounds with one aliphatic substituent containing 8 to 18 carbon atoms and another containing an anionic water-solubilizing group. Examples of are 3-(N,N-dimethyl-N-hexadecylammonio)propane-1-sulfonate and 3-(N,N-dimethyl-N-hexadecylammonio)-2-hydroxy propane-1-sulfonate.

C. EMULSIFIABLE CONCENTRATES

Emulsifiable concentrates are solutions in which the active materials and an emulsifying agent are dissolved in a non-watermiscible solvent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil-soluble petroleum sulfonates, or preferably mixtures of these emulsifying agents. Such emulsifying agents usually comprise about 1 to 10 weight percent of the total composition.

Typical emulsifiable concentrates contain about 15 to 50 weight percent active material, about 40 to 82 weight percent solvent, and about 1 to 10 weight percent emulsifier. Other additives such as spreading agents and stickers can also be included.

D. WETTABLE POWDERS

Wettable powders are water-dispersible compositions containing the active material, an inert solid extender, and one or more surfactants to provide rapid wetting and prevent flocculation when suspended in water.

Suitable solid extenders include both natural minerals and materials derived synthetically from such minerals. Examples include kaolinites, attapulgite clay, montmorillonite clays, synthetic silicas, synthetic magnesium silicate and calcium sulfate dihydrate.

Suitable surfactants include both nonionic and anionic types, and function as wetting agents and dispersants. Usually one of each is included. Preferred wetting agents are alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N(long chain acid) taurates.

Typical wettable powders contain 25 to 90 percent active material, 0.5 to 2.0 percent wetting agent, 0.25 to 5.0 percent dispersant, and from 9.25 to 74.25 weight percent inert extender. Frequently, 0.1 to 1.0 percent of the extender is replaced by a corrosion inhibitor and/or an antifoaming agent.

E. IN GENERAL

In general, any conventional postemergence method of application can be used, including common dusting or spraying equipment. The amount of active ingredient which is effective in producing the desired result, be it herbicidal or growth-regulating, depends on the nature of the plant species to be controlled and the prevailing conditions. Herbicidal effects are usually achieved at 0.1 to 50 pounds active ingredient per acre, preferably 1 to 10, while plant growth regulation is usually achieved at 0.1 to 20 pounds active ingredient per acre, preferably 0.5 to 5. It will be readily apparent to one skilled in the art that compounds of lower activity will require a higher dosage than more active compounds for the same degree of control.

What is claimed is:

1. A compound having the formula

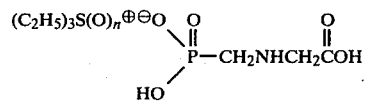

in which n is zero or one.

2. A compound according to claim 1 in which n is zero.

3. An herbicidal composition comprising an herbicidally effective amount of a compound having the formula

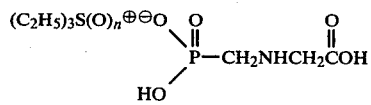

in which n is zero or one, and an inert diluent carrier.

4. A composition according to claim 3 in which n is zero.

5. A method of controlling undesirable vegetation comprising applying to the vegetation in postemergent state an herbicidal composition comprising an herbicidally effective amount of a compound having the formula

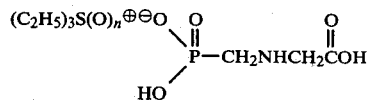

in which n is zero or one, and an inert diluent carrier.

6. A method according to claim 5 in which n is zero.

* * * * *